US011598781B2

(12) United States Patent
Bergmann et al.

(10) Patent No.: US 11,598,781 B2
(45) Date of Patent: Mar. 7, 2023

(54) METHOD FOR PREDICTING THE RISK OF INCIDENCE OF CHRONIC KIDNEY DISEASE

(71) Applicant: sphingotec GmbH, Hennigsdorf (DE)

(72) Inventors: Andreas Bergmann, Berlin (DE); Olle Melander, Limhamn (SE)

(73) Assignee: Sphingotec GmbH, Hennigsdorf (DE)

( * ) Notice: Subject to any disclaimer, the term of this patent is extended or adjusted under 35 U.S.C. 154(b) by 0 days.

(21) Appl. No.: 15/569,018

(22) PCT Filed: Apr. 21, 2016

(86) PCT No.: PCT/EP2016/058829
§ 371 (c)(1),
(2) Date: Oct. 24, 2017

(87) PCT Pub. No.: WO2016/170023
PCT Pub. Date: Oct. 27, 2016

(65) Prior Publication Data
US 2018/0128838 A1    May 10, 2018

(30) Foreign Application Priority Data
Apr. 24, 2015  (EP) .................................... 15165047

(51) Int. Cl.
*G01N 33/68* (2006.01)
*G01N 33/74* (2006.01)

(52) U.S. Cl.
CPC ......... *G01N 33/6893* (2013.01); *G01N 33/74* (2013.01); *G01N 2333/70* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| 8,013,123 B2 * | 9/2011 | Bergmann | ............. | C07K 16/26 |
| | | | | 424/130.1 |
| 9,664,695 B2 * | 5/2017 | Bergmann | ....... | G01N 33/54366 |
| 10,114,029 B2 * | 10/2018 | Bergmann | ....... | G01N 33/54366 |

FOREIGN PATENT DOCUMENTS

WO    WO-2014053501 A  *  4/2014   ....... G01N 33/54366

OTHER PUBLICATIONS

Waiker et al (J Am Soc Nephrol. Jan. 2012; 23(1):13-21) (Year: 2012).*
Mayeux (NeuroRx. Apr. 2004; 1(2):182-8) (Year: 2004).*
Sharain et al (Clin Appl Thromb Hemost. Jun. 2013;19(3):303-8. Epub Aug. 3, 2012) (Year: 2012).*
Araujo et al (Front Med (Lausanne). Oct. 10, 2017;4:168) (Year: 2017).*
Annual Physical Examinations from WebMD, downloaded from https://www.webmd.com/a-to-z-guides/annual-physical-examinations#1 on May 27, 2019 (Year: 2019).*
Johns Hopkins datasheet on End Stage Renal Disease (downloaded from https://www.hopkinsmedicine.org/health/conditions-and-diseases/end-stage-renal-failure on May 27, 2019) (Year: 2019).*

* cited by examiner

*Primary Examiner* — Brian Gangle
*Assistant Examiner* — Andrea K McCollum
(74) *Attorney, Agent, or Firm* — Millen, White, Zelano & Branigan, PC; Ryan Pool

(57) ABSTRACT

The present invention relates to means and methods suitable for risk prediction of chronic kidney disease (CKD) using Pro-Enkephalin or fragments thereof as biomarker. The risk prediction methods of the invention are intended for healthy subjects and for subjects suffering from diseases such as hypertension, cardiovascular diseases and events, diabetes, metabolic syndrome, obesity, or autoimmune diseases. Subject matter of the invention is also a method of predicting the worsening or improvement of kidney function or dysfunction in healthy and diseased individuals.

14 Claims, No Drawings

Specification includes a Sequence Listing.

SEQUENCE LISTING

<160> NUMBER OF SEQ ID NOS: 14

<210> SEQ ID NO 1
<211> LENGTH: 243
<212> TYPE: PRT
<213> ORGANISM: Homo sapiens

<400> SEQUENCE: 1

```
Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
    50                  55                  60

Lys Pro Glu Glu Ser His Leu Leu Ala Lys Arg Tyr Gly Gly Phe Met
65                  70                  75                  80

Lys Arg Tyr Gly Gly Phe Met Lys Lys Met Asp Glu Leu Tyr Pro Met
                85                  90                  95

Glu Pro Glu Glu Glu Ala Asn Gly Ser Glu Ile Leu Ala Lys Arg Tyr
            100                 105                 110

Gly Gly Phe Met Lys Lys Asp Ala Glu Glu Asp Ser Leu Ala Asn
            115                 120                 125

Ser Ser Asp Leu Leu Lys Glu Leu Leu Glu Thr Gly Asp Asn Arg Glu
    130                 135                 140

Arg Ser His His Gln Asp Gly Ser Asp Asn Glu Glu Glu Val Ser Lys
145                 150                 155                 160

Arg Tyr Gly Gly Phe Met Arg Gly Leu Lys Arg Ser Pro Gln Leu Glu
                165                 170                 175

Asp Glu Ala Lys Glu Leu Gln Lys Arg Tyr Gly Gly Phe Met Arg Arg
            180                 185                 190

Val Gly Arg Pro Glu Trp Trp Met Asp Tyr Gln Lys Arg Tyr Gly Gly
            195                 200                 205

Phe Leu Lys Arg Phe Ala Glu Ala Leu Pro Ser Asp Glu Glu Gly Glu
        210                 215                 220

Ser Tyr Ser Lys Glu Val Pro Glu Met Glu Lys Arg Tyr Gly Gly Phe
225                 230                 235                 240

Met Arg Phe
```

<210> SEQ ID NO 2
<211> LENGTH: 73
<212> TYPE: PRT
<213> ORGANISM: Homo sapiens

<400> SEQUENCE: 2

```
Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
    50                  55                  60

Lys Pro Glu Glu Ser His Leu Leu Ala
65                  70
```

<210> SEQ ID NO 3
<211> LENGTH: 5
<212> TYPE: PRT
<213> ORGANISM: Homo sapiens

<400> SEQUENCE: 3

Tyr Gly Gly Phe Met
1               5

<210> SEQ ID NO 4
<211> LENGTH: 5
<212> TYPE: PRT
<213> ORGANISM: Homo sapiens

<400> SEQUENCE: 4

Tyr Gly Gly Phe Leu
1               5

<210> SEQ ID NO 5
<211> LENGTH: 20
<212> TYPE: PRT
<213> ORGANISM: Homo sapiens

<400> SEQUENCE: 5

Met Asp Glu Leu Tyr Pro Met Glu Pro Glu Glu Glu Ala Asn Gly Ser
1               5                   10                  15

Glu Ile Leu Ala
            20

<210> SEQ ID NO 6
<211> LENGTH: 41
<212> TYPE: PRT
<213> ORGANISM: Homo sapiens

<400> SEQUENCE: 6

Asp Ala Glu Glu Asp Asp Ser Leu Ala Asn Ser Ser Asp Leu Leu Lys
1               5                   10                  15

Glu Leu Leu Glu Thr Gly Asp Asn Arg Glu Arg Ser His His Gln Asp
            20                  25                  30

Gly Ser Asp Asn Glu Glu Glu Val Ser
        35                  40

<210> SEQ ID NO 7
<211> LENGTH: 8
<212> TYPE: PRT
<213> ORGANISM: Homo sapiens

<400> SEQUENCE: 7

Tyr Gly Gly Phe Met Arg Gly Leu
1               5

<210> SEQ ID NO 8
<211> LENGTH: 12
<212> TYPE: PRT
<213> ORGANISM: Homo sapiens

<400> SEQUENCE: 8

Ser Pro Gln Leu Glu Asp Glu Ala Lys Glu Leu Gln
1               5                   10

<210> SEQ ID NO 9
<211> LENGTH: 11

```
<212> TYPE: PRT
<213> ORGANISM: Homo sapiens

<400> SEQUENCE: 9

Val Gly Arg Pro Glu Trp Trp Met Asp Tyr Gln
1               5                   10

<210> SEQ ID NO 10
<211> LENGTH: 22
<212> TYPE: PRT
<213> ORGANISM: Homo sapiens

<400> SEQUENCE: 10

Phe Ala Glu Ala Leu Pro Ser Asp Glu Glu Gly Glu Ser Tyr Ser Lys
1               5                   10                  15

Glu Val Pro Glu Met Glu
            20

<210> SEQ ID NO 11
<211> LENGTH: 29
<212> TYPE: PRT
<213> ORGANISM: Homo sapiens

<400> SEQUENCE: 11

Phe Ala Glu Ala Leu Pro Ser Asp Glu Glu Gly Glu Ser Tyr Ser Lys
1               5                   10                  15

Glu Val Pro Glu Met Glu Lys Arg Tyr Gly Gly Phe Met
            20                  25

<210> SEQ ID NO 12
<211> LENGTH: 7
<212> TYPE: PRT
<213> ORGANISM: Homo sapiens

<400> SEQUENCE: 12

Tyr Gly Gly Phe Met Arg Phe
1               5

<210> SEQ ID NO 13
<211> LENGTH: 8
<212> TYPE: PRT
<213> ORGANISM: Homo sapiens

<400> SEQUENCE: 13

Leu Lys Glu Leu Leu Glu Thr Gly
1               5

<210> SEQ ID NO 14
<211> LENGTH: 8
<212> TYPE: PRT
<213> ORGANISM: Homo sapiens

<400> SEQUENCE: 14

Ser Asp Asn Glu Glu Glu Val Ser
1               5
```

METHOD FOR PREDICTING THE RISK OF INCIDENCE OF CHRONIC KIDNEY DISEASE

SEQUENCE LISTING

The instant application contains a Sequence Listing which has been filed electronically in ASCII format and is hereby incorporated by reference in its entirety. Said ASCII copy, created on Oct. 22, 2018, is named BOEHMERP-0247_SL.txt and is 5,451 bytes in size.

The present invention relates to the field of kidney diseases, in particular to methods for the risk prediction of incidence of chronic kidney disease (CKD), or the risk of deterioration of kidney function in healthy or apparently healthy subjects (e.g. non-diabetic subjects, subjects without cardiovascular disease, etc.) or in subjects suffering from diseases such as hypertension, autoimmune disease, metabolic syndrome, diabetes, and/or cardiovascular disease, wherein the latter subjects do not suffer from CKD, using Pro-Enkephalin (PENK) as biomarker, the level of which is measured in the herein described methods.

With an estimated prevalence between 8-16% worldwide and expected disproportional growth in incidence in developing countries, CKD is becoming a growing public health issue. Commonly CKD is identified and staged by measuring the globular filtration rate (GFR) and albuminuria. Etiology of CKD is complex and it is believed that hypertension, diabetes and metabolic syndrome are involved in the pathophysiology. Kidney function has an impact on hemodynamic, vascular, inflammatory and metabolic disease due to its role in circulation and consequentially a decreased kidney function is associated with an increased risk of cardiovascular events, hospitalization and death. Thus, screening and early detection of decreased kidney function is important and therefore screening of certain risk groups, such as subjects with family predisposition as well as of patients with diabetes, hypertension, cardiovascular disease, autoimmune diseases and persons with structural disease of the renal tract is recommended. The commonly used markers for kidney function are creatinine and cystatin C. However, serum creatinine and estimated GFR (eGFR) are rather insensitive when it comes to identification of subjects at high risk of CKD. Therefore, there is a need for identification of novel and more sensitive biomarkers.

In 1975, enkephalins were the first endogenous opioids discovered. They are encoded by the PENK gene on chromosome 8 and similar to other neuropeptides, biosynthesis of the active enkephalins involves several steps including proteolytic cleavage of the precursor pre-protein Pro-Enkephalin (PENK), through which four copies of methionine-enkephalin and one copy of each leucine-enkephalin, a hexa- and an octa-peptide are processed. The precursor PENK is produced throughout the human body in neuronal as well as in non-neuronal cells. Although enkephalins have been discovered almost 40 years ago, their role has not been fully understood yet. In two earlier observational studies enkephalins have been implicated in kidney function. Recently, plasma levels of PENK were observed to associate with decreased eGFR and prognosis after acute myocardial infarction.

Previously, it was shown that the detection of Pro-Enkephalin may assist in (a) diagnosing or monitoring kidney function in a subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention. However, it was not known that Pro-Enkephalin serves as biomarker in the risk prediction for the development of chronic kidney disease in subjects that are healthy, apparently healthy, or patients with, e.g. metabolic syndrome, cardiovascular disease, autoimmune diseases, hypertension, diabetes, or subjects with an increased risk for the development of the latter conditions, but which do not suffer from kidney disease, in particular not from CKD.

Chronic Kidney Disease (CKD) can be distinguished from Acute Kidney Injury (AKI) and Acute Kidney Diseases (AKD), when certain functional and structural parameters are determined. Whereas CKD is characterized by a GFR of <60 ml/min per 1.73 $m^2$ for >3 months and by kidney damage for >3 months (Kidney International Supplements, 2013; Vol. 3: 19-62), in AKI no structural criteria are required, but an increase in serum creatinine (SCr) by 50% within 7 days, or an increase by 0.3 mg/dl (26.5 µmol/l), or oliguria is found. Further criteria for CKD (either of the following present for >3 months) are markers of kidney damage, e.g. albuminuria as a marker for increased glomerular permeability (albumin excretion rate [AER]≥30 mg/24 hours; albumin-to-creatinine ratio [ACR]≥30 mg/mmol); urinary sediment abnormalities (e.g. isolated non-visible (microscopic) hematuria with normal red blood cell (RBC) morphology (anisocytosis) in glomerular basement membrane (GBM) disorders, RBC casts in proliferative glomerulonephritis, WBS casts in pyelonephritis or interstitial nephritis, oval fat bodies or fatty casts in diseases with proteinuria); electrolyte and other abnormalities due to tubular disorders; abnormalities detected by histology or inferred (e.g. glomerular diseases such as diabetes, autoimmune diseases, drugs, neoplasia, vascular diseases such as artherosclerosis, hypertension, ischemia, vasculitis, thrombotic microangiopathy, tubulointerstitial diseases, e.g. infections, stones, obstruction, drug toxicity as well as cycstic and congenital diseases); structural abnormalities detected by imaging (ultrasound, computed tomography and magnetic resonance with or without isotope scans, angiography) such as polycystic kidneys, dysplastic kidneys, hydronephrosis due to obstruction, cortical scarring due to infarcts, pyelonephritis or associated with vesicoureteral reflux, renal masses or enlarged kidneys due to infiltrative diseases, renal artery stenosis, small and hyperechoic kidneys; and a history of kidney transplantation. Further, AKD is characterized by structural kidney damage for <3 months and by functional criteria that are also found in AKI, or a GFR of <60 ml/min per 1.73 $m^2$ for <3 months, or a decrease in GFR by ≥35%, or an increase in SCr by >50% for <3 months (Kidney International Supplements, Vol. 2, Issue 1, March 2012, pp. 19-36). A proper distinction between these different disease entities is important. The present invention surprisingly provides a new marker suitable for predicting the risk of incidence of CKD in healthy subjects, apparently healthy subjects, subjects with autoimmune and/or cardiovascular disease and/or hypertension and/or diabetes and/or metabolic syndrome. It is clear that an early detection of a potential risk in these patient groups would be of substantial benefit, in particular in measures that may be suitable to prevent the development of or further progression to CKD.

Subject matter of the present invention is a method for predicting the risk of incidence of chronic kidney disease (CKD) in a subject comprising:

a) determining the level of Pro-Enkephalin or fragments thereof in a bodily fluid obtained from said subject; and
b) correlating said level of Pro-Enkephalin or fragments thereof with a risk of incidence of CKD, wherein a level above a threshold is predictive for an enhanced risk of incidence of CKD, wherein the subject is selected from the group comprising
(i) healthy subjects,
(ii) diseased subjects not having CKD.

The subjects referred to in (i) and (ii) and in the methods for predicting the risk of incidence of CKD referred to herein below preferably have an estimated glomerular filtration rate (eGFR) of greater than 60 ml/min/1.73 m² for >3 months.

Subject matter of the present invention is a method for predicting the risk of incidence of CKD in a subject comprising:
determining the level of Pro-Enkephalin or fragments thereof in a bodily fluid obtained from said subject; and
correlating said level of Pro-Enkephalin or fragments thereof with a risk of incidence of CKD, wherein an elevated level is predictive for an enhanced risk of incidence of CKD,
wherein the subject is selected from a group comprising healthy subjects, apparently healthy subjects, subjects with a disease (e.g. metabolic syndrome, diabetes, obesity, cardiovascular disease or events, hypertension, and/or autoimmune disease, at the time the sample of bodily fluid is obtained from said subject, wherein said subject does not suffer from kidney disease.

Subject matter of the present invention is further a method for predicting the risk of incidence of CKD in a subject comprising:
determining the level of Pro-Enkephalin or fragments thereof in a bodily fluid obtained from said subject; and
correlating said level of Pro-Enkephalin or fragments thereof with a risk of incidence of CKD, wherein an elevated level is predictive for an enhanced risk of incidence of CKD,
wherein the subject has a diagnosis of an acute cardiovascular event or cardiovascular disease at the time the sample of bodily fluid is taken from said subject wherein said cardiovascular event is selected from the group comprising myocardial infarction, stroke, acute heart failure and wherein said subject does not suffer from kidney disease, and wherein the cardiovascular disease is selected from is selected from the group comprising coronary artery disease, cardiac disease associated with chronic or acute cerebrovascular disease, or from disease causing cardiac events such as arteriosclerosis, or heart failure, etc., wherein a subject afflicted by said cardiac disease does not suffer from kidney disease.

Subject matter of the present invention is also a method for predicting the risk of incidence of CKD in a subject comprising:
determining the level of Pro-Enkephalin or fragments thereof in a bodily fluid obtained from said subject; and
correlating said level of Pro-Enkephalin or fragments thereof with a risk of incidence of CKD, wherein an elevated level is predictive for an enhanced risk of incidence of CKD,
wherein the subject has a diagnosis of autoimmune disease at the time the sample of bodily fluid is taken from said subject, wherein said subject does not suffer from kidney disease.

Subject matter of the present invention is also a method for predicting the risk of incidence of CKD in a subject as defined in any of the preceding embodiments comprising:
determining the level of Pro-Enkephalin or fragments thereof in a bodily fluid obtained from said subject; and
correlating said level of Pro-Enkephalin or fragments thereof with a risk of incidence of CKD, wherein an elevated level is predictive for an enhanced risk of incidence of CKD,
wherein at least one additional parameter is determined, said parameter being selected from the group comprising: age, gender, systolic blood pressure and/or diastolic blood pressure (SBP and/or DBP), antihypertensive treatment (AHT), body mass index (BMI), body fat mass, body lean mass, waist circumference, waist-hip-ratio, current smoker, diabetes heredity, serum creatinine level, cystatin C level, cardiovascular disease (CVD), total cholesterol, triglyceride, low-density-lipocholesterol (LDL-C), high-density-lipocholesterol (HDL-C), whole blood or plasma glucose, plasma insulin, HOMA (Insulin (µU/ml)×Glucose (mmol/l)/22.5), and/or $HbA_{1c}$ (%), optionally further comprising determining the status of genetic markers.

Subject matter of the present invention is also a method for predicting the risk of incidence of CKD in a subject as defined in any of the preceding embodiments comprising:
determining the level of Pro-Enkephalin or fragments thereof in a bodily fluid obtained from said subject; and
correlating said level of Pro-Enkephalin or fragments thereof with a risk of incidence of CKD, wherein an elevated level is predictive for an enhanced risk of incidence of CKD,
wherein a group of clinical and laboratory parameters is determined, said group comprising: fasting glucose, systolic blood pressure, anti-hypertensive medication and body mass index.

Subject matter of the present invention is also a method for predicting the risk of incidence of CKD in a subject as defined in any of the preceding embodiments comprising:
determining the level of Pro-Enkephalin or fragments thereof in a bodily fluid obtained from said subject; and
correlating said level of Pro-Enkephalin or fragments thereof with a risk of incidence of CKD, wherein an elevated level is predictive for an enhanced risk of incidence of CKD,
wherein the Pro-Enkephalin fragment comprises Pro-Enkephalin A 119-159 (MR-PENK; SEQ ID NO: 6) or a fragment thereof or MR-PENK comprising fragments. MR-PENK or fragments thereof or MR-PENK comprising fragments may be determined using an immunoassay or a mass spectrometric method.

Subject matter of the present invention is also a method for predicting the risk of incidence of CKD in a subject as defined in any of the preceding embodiments comprising:
determining the level of Pro-Enkephalin or fragments thereof in a bodily fluid obtained from said subject; and
correlating said level of Pro-Enkephalin or fragments thereof with a risk of incidence of CKD, wherein an elevated level is predictive for an enhanced risk of incidence of CKD,
wherein said method is performed at least once at time-point t0 and optionally at least one or more subsequent time-point(s) (t1 . . . tn) to monitor the risk development of incidence of CKD.

Subject matter of the present invention is also a method for predicting the risk of incidence of CKD in a subject as defined in any of the preceding embodiments comprising:
determining the level of Pro-Enkephalin or fragments thereof in a bodily fluid obtained from said subject; and correlating said level of Pro-Enkephalin or fragments thereof with a risk of incidence of CKD, wherein an elevated level is predictive for an enhanced risk of incidence of CKD, wherein a bodily fluid of a subject with a Pro-Enkephalin level above a certain threshold level, optionally compared with the mean value of Pro-Enkephalin in demonstrably healthy subjects, is classified as having an elevated risk for development of CKD. According to the invention, said threshold associated with an elevated risk for development of CKD may be between 30 and 80 pmol/L, more preferably between 35 and 60 pmol/L, even more preferably between 40 and 50 pmol/L, most preferred between 41 and 49 pmol/L.

Subject matter of the present invention is also a method for predicting the risk of incidence of CKD in a subject as defined in any of the preceding embodiments comprising:

determining the level of Pro-Enkephalin or fragments thereof in a bodily fluid obtained from said subject; and correlating said level of Pro-Enkephalin or fragments thereof with a risk of incidence of CKD, wherein an elevated level is predictive for an enhanced risk of incidence of CKD, further comprising performing a step of selecting suitable therapeutic or preventive measures, when the level Pro-Enkephalin or fragments thereof is above a threshold, preferably a threshold associated with an elevated risk for development of CKD may be between 30 and 80 pmol/L, more preferably between 35 and 60 pmol/L, even more preferably between 40 and 50 pmol/L, most preferred between 41 and 49 pmol/L.

Subject matter of the present invention is also a method for predicting a worsening or an improvement of kidney function or dysfunction in (i) healthy subjects, or (ii) diseased subjects with or without kidney dysfunction, wherein said method comprises the steps of (a) determining the level of Pro-Enkephalin or fragments thereof in a bodily fluid obtained from said subject; and (b) correlating said level of Pro-Enkephalin or fragments thereof with a risk of worsening or improvement of kidney function or dysfunction, wherein a level above a threshold is predictive for an enhanced risk of worsening of kidney function or dysfunction in patient groups (i) or (ii). According to the invention, said threshold associated with an elevated risk of worsening or improvement of kidney function or dysfunction may be between 30 and 80 pmol/L, more preferably between 35 and 60 pmol/L, even more preferably between 40 and 50 pmol/L, most preferred between 41 and 49 pmol/L.

The subject may be selected from a group comprising healthy subjects, e.g. those with an eGFR of greater than 90 ml/min/1.73 m$^2$ or greater than 60 ml/min/1.73 m$^2$, apparently healthy subjects, e.g. those with an eGFR of greater than 90 ml/min/1.73 m$^2$ or greater than 60 ml/min/1.73 m$^2$, subjects with a disease (e.g. with metabolic syndrome, diabetes, obesity, cardiovascular disease or events as defined herein, hypertension, autoimmune disease as defined herein at the time the sample of bodily fluid is obtained from said subject, wherein said subject does not suffer from kidney disease. The group of subjects (ii) that may be analyzed using the method above comprises also those with acute kidney injury (AKI). Acute kidney injury encompasses a wide spectrum of injury to the kidneys, not just kidney failure. AKI-patients subjected to the methods for predicting a worsening or an improvement of kidney function or dysfunction referred to in the context of the herein described embodiments comprise those with chronic kidney disease (adults with an eGFR less than 60 ml/min/1.73 m$^2$), heart failure, liver disease, diabetes, history of acute kidney injury, oliguria (urine output less than 0.5 ml/kg/hour), neurological or cognitive impairment or disability, which may mean limited access to fluids because of reliance on a carer, hypovolemia, use of drugs with nephrotoxic potential (such as non-steroidal anti-inflammatory drugs [NSAIDs], aminoglycosides, angiotensin-converting enzyme [ACE] inhibitors, angiotensin II receptor antagonists [ARBs] and diuretics) within the past week, especially if hypovolemic, use of iodinated contrast agents within the past week, symptoms or history of urological obstruction, or conditions that may lead to obstruction, sepsis, deteriorating early warning scores, age 65 years or over, hypertension. As used herein, the term "worsening of kidney function or dysfunction" means the transition from a less severe grade of AKI according to the RIFLE criteria to a more severe grade, which includes separate criteria for serum creatinine and urine output (UO). In terms of serum creatinine criteria this means a transition from the "Risk stage" (increased creatinine×1.5) to the "Injury stage" (increased creatinine×2), or further to the "Failure stage" (increased creatinine×3 or creatinine>4 mg/dL) or worse, optionally accompanied by a decrease of the eGFR. As used herein, the term "improvement of kidney function or dysfunction" means the transition in the opposite direction, e.g. from the "Failure stage" to the "Risk stage" or better.

Subject matter of the present invention is also a method as defined in the preceding paragraph, wherein at least one additional parameter is determined, said parameter being selected from the group comprising: age, gender, systolic blood pressure and/or diastolic blood pressure (SBP and/or DBP), antihypertensive treatment (AHT), body mass index (BMI), body fat mass, body lean mass, waist circumference, waist-hip-ratio, current smoker, diabetes heredity, serum creatinine level, cystatin C level, cardiovascular disease (CVD), total cholesterol, triglyceride, low-density-lipocholesterol (LDL-C), high-density-lipocholesterol (HDL-C), whole blood or plasma glucose, plasma insulin, HOMA (Insulin (µU/ml)×Glucose (mmol/l)/22.5), and/or HbA1c (%), optionally further comprising determining the status of genetic markers. In one sub-embodiment of the present invention relating to a method as defined in the preceding paragraph said group comprising: fasting glucose, systolic blood pressure, anti-hypertensive medication and BMI. The level of Pro-Enkephalin or fragments thereof may be determined by an immunoassay or using any other suitable methods, e.g. a mass spectrometry assay. In said methods PENK or MR-PENK (SEQ ID NO: 6) or a fragment thereof as defined in the present disclosure may be used as target of the immunoassay.

Subject matter of the present invention is also a method for predicting a worsening or an improvement of kidney function or dysfunction as described in the foregoing paragraphs, wherein said method is performed at least once at time-point t0 and optionally at least one or more subsequent time-point(s) (t1 . . . tn) to monitor worsening or improvement of kidney function or dysfunction.

Subject matter of the present invention is also a method for predicting a worsening or an improvement of kidney function or dysfunction as described in the foregoing paragraphs, wherein a bodily fluid of a subject with a Pro-Enkephalin level above a certain threshold level, optionally compared with the mean value of Pro-Enkephalin in demonstrably healthy subjects, is investigated.

Subject matter of the present invention is also a method for predicting a worsening or an improvement of kidney function or dysfunction as described in the foregoing paragraphs, wherein a binder specifically binding PENK or a fragment thereof is selected from the group comprising an antibody, an antibody fragment or a non-Ig-Scaffold binding to Pro-Enkephalin or fragments thereof. In these methods it is also possible to use an assay comprising two binders that bind to two different regions within the amino acid sequence of Pro-Enkephalin [SEQ ID No. 1]. In a preferred embodiment of the invention said two binders bind to two different regions within the amino acid sequence of MR-PENK [SEQ ID No. 6]. In the most preferred embodiment of the invention said two binders bind to two different regions within the amino acid sequence of MR-PENK [SEQ ID No. 6] that is amino acid 133-140 (SEQ ID NO. 13) and amino acid 152-159 (SEQ ID No. 14) wherein each of said regions comprises at least 4 or 5 amino acids.

Subject matter of the present invention is also a method for predicting a worsening or an improvement of kidney function or dysfunction as described in the foregoing paragraphs, wherein an assay is used for determining the level of Pro-Enkephalin or fragments thereof as defined in the present disclosure.

Subject matter of the present invention is also a method for predicting a worsening or an improvement of kidney function or dysfunction as described in the foregoing paragraphs, further comprising performing a step of selecting suitable therapeutic or preventive measures, when the level Pro-Enkephalin or fragments thereof is above a threshold, preferably a threshold between 30 and 80 pmol/L, more preferably between 35 and 60 pmol/L, even more preferably between 40 and 50 pmol/L, most preferred between 41 and 49 pmol/L.

Subject matter of the present invention is also a method for predicting a worsening or an improvement of kidney function or dysfunction as described in the foregoing paragraphs, wherein said determination of Pro-Enkephalin or fragments thereof is performed more than once.

Subject matter of the present invention is also a method for predicting the risk of incidence of CKD as defined in any of the preceding paragraphs, wherein said healthy or apparently subject has as an eGFR of greater than 60 ml/min/1.73 m$^2$ at baseline. In the context of the present invention, the term "healthy" means that the subject in question does not suffer from any disease. In the context of the present invention, the term "apparently healthy" means that the subject in question does not suffer from any diagnosed disease, or has a diagnosis of a disease or disorder that is different from the herein specified diseases, i.e. hypertension, cardiovascular disease, metabolic syndrome, diabetes, and/or autoimmune disease, and does not suffer from kidney disease. The term "healthy subject" includes also the group of subjects that are voluntary organ donors, e.g. subjects that are potential kidney transplant donors. These donors may be tested in accordance with the methods of the present invention to exclude those subjects as kidney transplant donors that have an increased risk of incidence of chronic kidney disease.

As used herein, the term "autoimmune disease" relates to a disease that arises from an abnormal immune response of the body against substances and tissues normally present in the body, wherein the autoimmune disease is selected from the group comprising Sjögren's disease; autoimmune diseases of the kidneys, e.g. SLE, autoimmune degenerative diseases of joints, particularly rheumatoid arthritis; or autoimmune diseases of the central nervous system, e.g. multiple sclerosis, autoimmune diseases of the skin, e.g. psoriasis, and any other autoimmune disease.

Subject matter of the present invention is also a method for predicting the risk of incidence of CKD as defined in any of the preceding paragraphs, wherein additionally at least one clinical parameter is determined selected from the group comprising age, gender, systolic blood pressure and/or diastolic blood pressure (SBP and/or DBP), antihypertensive treatment (AHT), body mass index, body fat mass, body lean mass, waist circumference, waist-hip-ratio, current smoker, diabetes heredity, serum creatinine level, cystatin C level, and previous cardiovascular disease (CVD). Furthermore, it is contemplated that additional parameters are determined, e.g. total cholesterol (mmol/L), triglyceride (mmol/L), low-density-lipocholesterin (LDL-C) (mmol/L), high-density-lipocholesterin (HDL-C) (mmol/L), whole blood glucose (mmol/L), plasma insulin (mIU), HOMA (insulin*glucose/22.5), and/or HbA$_{1c}$ (%). Furthermore, it is contemplated that the status of genetic markers is analysed using, e.g., a genome-wide analysis. Still further, it is contemplated to measure the following parameters in combination: Pro-Enkephalin level, fasting glucose, systolic blood pressure, anti-hypertensive medication and BMI in the herein described methods for the risk prediction of CKD.

In one embodiment of the invention the sample is selected from the group comprising a blood sample, a serum sample, a plasma sample, a cerebrospinal fluid (CSF) sample, a saliva sample and a urine sample or an extract of any of the aforementioned samples.

Pro-Enkephalin or fragments thereof may be measured in samples from non-fastening or fastening subjects. Fastening level means no food uptake 10 hours or preferably 12 hours prior blood sampling.

Subject matter of the present invention is also a method for predicting the risk of incidence of CKD as defined in any of the preceding paragraphs, wherein the level of Pro-Enkephalin or fragments thereof having at least a length of 5 amino acids, or at least 6 amino acids, or at least 7 amino acids, or at least 8 amino acids, or at least 9 amino acids, or at least 10 amino acids, or at least 12 amino acids is determined by a diagnostic assay, preferably by an immunoassay. The Pro-Enkephalin fragment may comprise Pro-Enkephalin 119-159 (SEQ ID No. 6) or be a suitable fragment thereof having the above indicated lengths.

Subject matter of the present invention is also a method for predicting the risk of incidence of CKD as defined in any of the preceding paragraphs, wherein said method is performed more than once in order to monitor the risk of incidence of CKD. Said monitoring may be performed in order to evaluate the response of said subject to preventive and/or therapeutic measures taken.

Subject matter of the present invention is also a method for predicting the risk of incidence of CKD as defined in any of the preceding paragraphs, wherein said method is performed in order to stratify said subjects into risk groups as further defined below. In specific embodiments of the invention the methods are used in order to stratify the subjects into CKD risk groups, e.g. those with a low risk, medium risk, or high risk to develop CKD. Low risk for the development of CKD means that the Pro-Enkephalin value is substantially not elevated compared to a predetermined value in healthy subjects who did not develop CKD. A medium risk exists when the level of Pro-Enkephalin is elevated compared to a predetermined value in healthy subjects who did not develop CKD, and a high risk exists when the level of Pro-Enkephalin is significantly elevated at baseline measurement and continues to increase at subsequent analysis. Irrespective of the elevated or significantly elevated level, the subject may not have a decreased eGFR (i.e. the eGFR is >60 ml/min/1.73 m$^2$).

Subject matter of the present invention is also a method for predicting the risk of incidence of CKD as defined in any of the preceding paragraphs, wherein a bodily fluid of a subject with an "elevated level" of Pro-Enkephalin or a fragment thereof as disclosed herein has a level above a certain threshold level.

The term fragment of PENK designates any fragment that can be detected in any of the herein described methods, e.g. using an immunoassay or any other method, such as spectrometry, e.g. mass spectrometry. Preferably, the fragments have a length of at least 5 amino acids, or at least 6 amino acids, or at least 7 amino acids, or at least 8 amino acids, or at least 9 amino acids, or at least 10 amino acids, or at least 12 amino acids. Specific fragments are also disclosed in the sequence listing and comprise, e.g. MR-PENK and fragments thereof, MR-PENK comprising fragments that may be detected using the herein described methods, assays and binders.

The expressions "elevated level" means a level above a certain threshold level.

Threshold levels may be determined by measuring samples from subjects who did develop a certain condition (e.g. CKD) and samples from subjects who did not develop the condition. One possibility to determine a threshold is the calculation of receiver operating characteristic curves (ROC curves), plotting the value of a variable versus its relative frequency in the "normal" population (e.g. subjects who did not develop the condition of obesity) and "disease" population (e.g. subjects who did develop the condition of obesity). A distribution of the marker levels for subjects developing or not developing a certain condition will likely overlap. Under such conditions, a test does not absolutely distinguish "normal" from "disease" with 100% accuracy, and the area of overlap indicates where the test cannot distinguish normal from "disease". A threshold is selected, above which (or below which, depending on how a marker changes with the "disease") the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (Hanley et al. 1982. *Radiology* 143: 29-36). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement. The horizontal axis of the ROC curve represents (1—specificity), which increases with the rate of false positives. The vertical axis of the curve represents sensitivity, which increases with the rate of true positives. Thus, for a particular cut-off selected, the value of (1—specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test. The odds ratio is a measure of effect size, describing the strength of association or non-independence between two binary data values (e.g. the ratio of the odds of an event occurring in test negative group to the odds of it occurring in the test positive group).

Threshold levels can be obtained for instance from a Kaplan-Meier analysis, where the occurrence of a disease or the probability of a serious condition and/or death is correlated with the e.g. quartiles of the respective markers in the population. According to this analysis, subjects with marker levels above the 75th percentile have a significantly increased risk for getting the diseases according to the invention. This result is further supported by Cox regression analysis with adjustment for classical risk factors. The highest quartile versus all other subjects is highly significantly associated with increased risk for getting a disease or the probability of a serious condition and/or death according to the invention.

Other preferred cut-off values are for instance the 90th, 95th or 99th percentile of a reference population. By using a higher percentile than the 75th percentile, one reduces the number of false positive subjects identified, but one might miss to identify subjects, who are at moderate, albeit still increased risk. Thus, one might adapt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

The person skilled in the art knows how to determine such statistically significant levels.

Subject matter of the present invention is also a point-of-care device for performing a method comprising the steps (a) determining the level of Pro-Enkephalin or fragments thereof in a bodily fluid obtained from said subject; and (b) correlating said level of Pro-Enkephalin or fragments thereof with a risk of incidence of CKD, wherein an elevated level is predictive for an enhanced risk of incidence of CKD, referred to in any of the preceding paragraphs. Said point-of-care device may also be used in methods for predicting a worsening or improvement of kidney function or dysfunction as defined in the above disclosure.

Subject matter of the present invention is the use of Pro-Enkephalin (PENK) or fragments thereof as marker in the prediction of the risk for a subject to develop CKD in healthy and diseased subjects. Surprisingly, it has been shown that PENK or fragments are powerful and highly significant biomarkers in the prediction of the risk of developing CKD.

According to the present invention the immunoreactive analyte used in the herein described methods is not leu-enkephalin and not met-enkephalin. In a specific embodiment said immunoreactive analyte is mid-regional-Pro-Enkephalin (MR-PENK) or a fragment thereof having at least 5 amino acids. Therefore, when a binder is used in the methods of the present invention that binds to a region within the amino acid sequence of Pro-Enkephalin (PENK) in a bodily fluid the terms "determining the level of PENK or fragments thereof of at least 5 amino acids in a bodily fluid obtained from said subject" are equivalent to "determining the level of immunoreactive analyte by using at least one binder that binds to a region within the amino acid sequence of PENK in a bodily fluid obtained from said subject". In a specific embodiment a binder is used in the methods of the present invention that binds to a region within the amino acid sequence of PENK in a bodily fluid. In a specific embodiment said binder used in the methods of the present invention does not bind to a region within the amino acid sequence of Leu-Enkephalin or Met-Enkephalin in a bodily fluid. In another specific embodiment of the present invention said at least one binder binds to MR-PENK or a fragment thereof having at least 5 amino acids.

The term "subject" as used herein refers to a living human or non-human organism. Preferably herein the subject is a human subject. The subject may be healthy, apparently healthy, it may be a diseased subject without CKD, or—if not stated otherwise—may have a diagnosis of clinically manifested disorder or disease selected from the group comprising hypertension, obesity, cardiovascular diseases, metabolic syndrome, diabetes, and autoimmune diseases.

As used in connection with the preceding embodiments, an increased concentration of Pro-Enkephalin or fragments thereof indicates a risk for the development of CKD in subjects that are healthy, apparently healthy, or have a diagnosis of the herein referred disorders or diseases, but that do not have CKD. In embodiments of the present invention, the risk for development of CKD is increased when the subject has increased concentration of Pro-Enkephalin or fragments thereof and at the same time has an eGFR of >60 ml/min/1.73 m$^2$. In further embodiments, the risk for development of CKD is increased when the subject has increased concentration of Pro-Enkephalin or fragments thereof and at the same time has an eGFR of >60 ml/min/1.73 m$^2$ and the subject has a decline in fasting glucose and/or increase of plasma cystatin C and/or creatinine, when the herein described methods are repeated. For example, when a patient has an increased concentration of Pro-Enkephalin or fragments thereof and at the same time has an eGFR of >60 ml/min/1.73 m$^2$ at baseline (t0), and has an increased concentration of Pro-Enkephalin or fragments thereof and at the same time has an eGFR of >60 ml/min/1.73 m$^2$ and shows a decline in fasting glucose and/or increase of plasma cystatin C and/or creatinine at one or more later point(s) in time (t1, t2, . . . tn), the risk for development of CKD increases. In other words, the development of risk incidence can be monitored using the herein described methods.

Further, a reduction of the eGFR over a certain time period in combination with an increase of the level of Pro-Enkephalin or fragments thereof, optionally accompanied by a decline in fasting glucose and/or increase of plasma cystatin C and/or creatinine at one or more later point(s) in time (t1, t2 . . . tn) can be determined using the herein described methods. A further increase of the level of Pro-Enkephalin or fragments thereof, optionally accompanied by a decline in fasting glucose and/or increase of plasma cystatin C and/or creatinine over time is associated with an increased risk for the development of CKD.

According to the methods of the present invention, subsequent to a baseline measurement (t0) additional measurements (t1 to tn) may be performed as required, e.g. every month, in intervals of 2 months, 3 months, 6 months, 12 months, 24 months, etc. The intervals between two measurements do not have to be identical. For example, when an elevated level of Pro-Enkephalin is measured at baseline (t0) in a subject while the eGFR is >60 ml/min/1.73 m$^2$, the next measurement (t1) may be shortly after t0 in order to verify, whether or not the level of Pro-Enkephalin decreases, remains at an elevated level or even increases and corresponding medical interventions are desired, i.e. agents taken to lower the blood pressure, lowering protein intake, lowering salt intake, optionally administering agents to lower serum uric acid concentrations, and/or a modification of certain lifestyle habits, e.g. a diet considering a suitable salt, phosphate, potassium, and protein intake where indicated, the reduction of weight, achieving a healthier weight (BMI 20-25, according to country specific demographics), stop smoking, undertaking physical activities compatible with cardiovascular health and tolerance, etc. Similarly, when the measurement of important co-factors that are associated with an increased risk of development of CKD show a decline in fasting glucose and/or increase of plasma cystatin C and/or creatinine, the measurements according to any of the methods disclosed herein should be repeated in shorter intervals to monitor development of these factors and of the level of Pro-Enkephalin or fragments thereof.

Again, on the basis of the results obtained in the measurements of Pro-Enkephalin or fragments thereof, a suitable medical intervention as disclosed above may be performed and/or a modification of certain lifestyle habits, the reduction of weight, anti-hypertensive treatment, treatment with anti-diabetic drugs, with immune-modulating drugs (e.g. methotrexate, corticosteroids, biologicals, for example antibodies or other binders or modulators that target immune cells or cytokines involved in calibrating the immune response such as IL-6, IL-2 (Adalimumbab, Namilumab, etc.)). Therefore, the present invention not only relates to measurement methods for prediction of risk incidence in the herein described subjects, but concerns also methods of treatment or prevention of disorders, diseases or clinical conditions which may increase the risk for development of CKD, if not adequately treated. The therapy or intervention supporting or replacing kidney function may comprise various methods of renal replacement therapy including but not limited to hemodialysis, peritoneal dialysis, hemofiltration and renal transplantation.

During follow up measurements, a relative change of Pro-Enkephalin or fragments thereof correlates with the improvement (lowering Pro-Enkephalin or fragments thereof) and with the worsening (increased Pro-Enkephalin or fragments thereof) of the risk of development of CKD.

Pro-Enkephalin or fragments thereof are superior in comparison to other markers for kidney function/dysfunction diagnosis and follow up (NGAL, blood creatinine, creatinine clearance, Cystatin C, Urea). Superiority means higher specificity, higher sensitivity and better correlation to clinical endpoints. Also in this aspect, Pro-Enkephalin or fragments thereof are superior to above mentioned clinical markers.

In one embodiment of the invention it should be understood that the term fragments of Pro-Enkephalin also include Leu-Enkephalin and Met-Enkephalin.

Subject matter according to the present invention are also methods wherein the level of Pro-Enkephalin or fragments thereof of at least 5 amino acids is determined by using a binder, at least one binder, to Pro-Enkephalin or fragments thereof of at least 5 amino acids. In one embodiment of the invention said binder is selected from the group comprising an antibody, an antibody fragment or a non-Ig-Scaffold binding to Pro-Enkephalin or fragments thereof of at least 5 amino acids. In a specific embodiment said at least one binder binds to a region with the sequences selected from the group comprising SEQ ID No. 1, 2, 3, 4, 5, 6, 7, 8, 9 and 10. In a specific embodiment said binder do not bind to enkephalin peptides Met-Enkephalin (SEQ ID No: 3), and Leu-Enkephalin (SEQ ID No: 4).

In a specific embodiment said at least one binder binds to a region within the sequences selected from the group comprising SEQ ID No. 1, 2, 5, 6, 7, 8, 9 and 10. In another specific embodiment said at least one binder binds to a region with the sequences selected from the group comprising SEQ ID No. 2, 5, 6, and 10. In another very specific embodiment said binder bind to Pro-Enkephalin 119-159, Mid-regional Pro-Enkephalin-fragment, MR-PENK (SEQ ID No. 6).

Pro-Enkephalin has the following sequence:

```
(Pro-Enkephalin (1-243)
                                          SEQ ID NO: 1
ECSQDCATCSYRLVRPADINFLACVMECEGKLPSLKIWETCKELLQLSKP

ELPQDGTSTLRENSKPEESHLLAKRYGGFMKRYGGFMKKMDELYPMEPEE

EANGSEILAKRYGGFMKKDAEEDDSLANSSDLLKELLETGDNRERSHHQD

GSDNEEEVSKRYGGFMRGLKRSPQLEDEAKELQKRYGGFMRRVGRPEWWM

DYQKRYGGFLKRFAEALPSDEEGESYSKEVPEMEKRYGGFMRF
```

Fragments of Pro-Enkephalin that may be determined in a bodily fluid may be selected, e.g., from the group of the following fragments:

```
SEQ ID NO: 2 (Synenkephalin, Pro-Enkephalin 1-73)
ECSQDCATCSYRLVRPADINFLACVMECEGKLPSLKIWETCKELLQLSKP

ELPQDGTS

TLRENSKPEESHLLA

SEQ ID NO: 3 (Met-Enkephalin)
YGGFM

SEQ ID NO: 4 (Leu-Enkephalin)
YGGFL

SEQ ID NO: 5 (Pro-Enkephalin 90-109)
MDELYPMEPEEEANGSEILA

SEQ ID NO 6: (Pro-Enkephalin 119-159,
Mid-regional Pro-Enkephalin-fragment, MR-PENK)
DAEEDDSLANSSDLLKELLETGDNRERSHHQDGSDNEEEVS SEQ ID NO: 7 (Met-Enkephalin-Arg-Gly-Leu)
YGGFMRGL SEQ ID NO: 8 (Pro-Enkephalin 172-183)
SPQLEDEAKELQ SEQ ID NO: 9 (Pro-Enkephalin 193-203)
VGRPEWWMDYQ SEQ ID NO: 10 (Pro-Enkephalin 213-234)
FAEALPSDEEGESYSKEVPEME SEQ ID NO: 11 (Pro-Enkephalin 213-241)
FAEALPSDEEGESYSKEVPEMEKRYGGF M SEQ ID NO: 12 (Met-Enkephalin-Arg-Phe)
YGGFMRF
```

Determining the level of Pro-Enkephalin or fragments thereof including Leu-Enkephalin and Met-Enkephalin may mean that the immunoreactivity towards Pro-Enkephalin or fragments thereof including Leu-Enkephalin and Met-Enkephalin is determined. A binder used for determination of Pro-Enkephalin or fragments thereof including Leu-Enkephalin and Met-Enkephalin depending of the region of binding may bind to more than one of the above displayed molecules. This is clear to a person skilled in the art. Thus, according to the present invention the level of immunoreactive analyte by using at least one binder that binds to a region within the amino acid sequence of any of the above peptide and peptide fragments, (i.e. Pro-Enkephalin and fragments according to any of the sequences in SEQ ID NOs: 1 to 12), is determined in a bodily fluid obtained from said subject; and correlated to the specific embodiments of clinical relevance.

In a more specific embodiment of the methods according to the present invention the level of MR-PENK is determined (SEQ ID NO. 6: Pro-Enkephalin 119-159, Mid-regional Pro-Enkephalin-fragment, MR-PENK).

In a more specific embodiment the level of immunoreactive analyte is determined using at least one binder that binds to MR-PENK and is subsequently correlated to the above mentioned embodiments of the invention to the specific embodiments of clinical relevance, e.g. correlating said level of immunoreactive analyte with the risk of development of CKD in a subject. Alternatively the level of any of the above analytes may be determined by other analytical methods e.g. mass spectroscopy.

In a specific embodiment the level of immunoreactive analyte is determined by using at least one binder that binds to a region within the amino acid sequence of a peptide selected from the group comprising Pro-Enkephalin or fragments thereof of at least 5 amino acids, or at least 6 amino acids, or at least 7 amino acids, or at least 8 amino acids, or at least 9 amino acids, or at least 10 amino acids, or at least 12 amino acids. In a specific embodiment said at least one binder binds to a region with the sequences selected from the group comprising SEQ ID No. 1, 2, 3, 4, 5, 6, 7, 8, 9 and 10.

In a specific embodiment said binder do not bind to enkephalin peptides Met-Enkephalin as depicted in SEQ ID No: 3, and Leu-Enkephalin depicted in SEQ ID No: 4.

In a specific embodiment said at least one binder binds to a region with the sequences selected from the group comprising SEQ ID No. 1, 2, 5, 6, 7, 8, 9 and 10.

In another specific embodiment said at least one binder binds to a region with the sequences selected from the group comprising SEQ ID No. 2, 5, 6, and 10.

In another very specific embodiment said binder binds to Pro-Enkephalin 119-159, Mid-regional Pro-Enkephalin-fragment, MR-PENK (SEQ ID No. 6).

The afore-mentioned binder binds to said peptides in a bodily fluid obtained from said subject. In one embodiment of the invention said binder is selected from the group comprising an antibody, an antibody fragment or a non-Ig-Scaffold binding to Pro-Enkephalin or fragments thereof of at least 5 amino acids, or at least 6 amino acids, or at least 7 amino acids, or at least 8 amino acids, or at least 9 amino acids, or at least 10 amino acids, or at least 12 amino acids.

In a more specific embodiment the level of immunoreactive analyte by using at least one binder that binds to a region within the amino acid sequence of Pro-Enkephalin 119-159, Mid-regional Pro-Enkephalin-fragment, MR-PENK (SEQ ID No. 6) in a bodily fluid is obtained from said subject.

In a specific embodiment the level of Pro-Enkephalin or fragments thereof is measured with an immunoassay using antibodies or fragments of antibodies binding to Pro-Enkephalin or fragments thereof. An immunoassay that may be useful for determining the level of Pro-Enkephalin or fragments thereof of at least 5 amino acids may comprise the steps as used in the Examples and referred to in the claims. All thresholds and values have to be seen in correlation to the test and the calibration used according to the Examples. A person skilled in the art may know that the absolute value of a threshold might be influenced by the calibration used. This means that all values and thresholds given herein are to be understood in context of the calibration used.

According to the invention the binder to Pro-Enkephalin or fragments thereof is selected from the group consisting of antibodies, e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the $CH_3$ domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multi specific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulins. In preferred embodiments, the binders are antibodies that were prepared as set forth in PCT application PCT/EP2013/070470.

In a specific embodiment the level of Pro-Enkephalin or fragments thereof is measured with an assay using binders selected from the group comprising aptamers, non-Ig scaffolds as described in greater detail below binding to Pro-Enkephalin or fragments thereof. Binders that may be used for determining the level of Pro-Enkephalin or fragments thereof exhibit an affinity constant to Pro-Enkephalin of at least $10^7$ $M^{-1}$, preferred $10^8 M^{-1}$, preferred affinity constant is greater than $10^9$ $M^{-1}$, most preferred greater than $10^{10}$ $M^{-1}$. A person skilled in the art knows that it may be considered to compensate lower affinity by applying a higher dose of compounds and this measure would not lead out-of-the-scope of the invention. Binding affinity may be determined using the Biacore method, offered as service analysis e.g. at Biaffin, Kassel, Germany.

A human Pro-Enkephalin-control sample is available by ICI-Diagnostics, Berlin, Germany http://www.ici-diagnostics.com/. The assay may also be calibrated by synthetic (for our experiments we used synthetic MR-PENK, SEQ ID NO. 6) or recombinant Pro-Enkephalin or fragments thereof.

In addition to antibodies other biopolymer scaffolds are well known in the art to complex a target molecule and have been used for the generation of highly target specific biopolymers. Examples are aptamers, spiegelmers, anticalins and conotoxins. Non-Ig scaffolds may be protein scaffolds and may be used as antibody mimics as they are capable to bind to ligands or antigenes. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds (e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

The threshold for predicting the risk of incidence of CKD may be between 30 and 80 pmol/L MR-PENK, more preferably between 35 and 60 pmol/L, even more preferably between 40 and 50 pmol/L, most preferred between 41 and 49 pmol/L.

In one specific embodiment the level of Pro-Enkephalin is measured with an immunoassay and said binder is an antibody or an antibody fragment binding to Pro-Enkephalin or fragments thereof of at least 5 amino acids.

In one specific embodiment the assay used comprises two binders that bind to two different epitope within Pro-Enkephalin that comprises amino acids 133-140 (SEQ ID No. 13) and amino acids 152-159 (SEQ ID NO. 14) wherein each of said epitopes comprises at least 4, 5, 6, 7 or 8 amino acids.

In one embodiment the sensitivity of said assay for determining Pro-Enkephalin or fragments thereof is <15 pmol/L, preferably <10 pmol/L and more preferably <6 pmol/L.

Subject matter of the present invention is the use of at least one binder that binds to an epitope within the amino acid sequence of a peptide selected from the group comprising the peptides and fragments of SEQ ID No. 1 to 12 in a bodily fluid obtained from said subject in a method of predicting or monitoring the risk of development of CKD.

In one embodiment of the invention said binder is selected from the group comprising an antibody, an antibody fragment or a non-Ig-Scaffold binding to Pro-Enkephalin or fragments thereof of at least 5 amino acids. In a specific embodiment said at least one binder binds to an epitope with the sequences selected from the group comprising SEQ ID NOs: 1, 2, 3, 4, 5, 6, 7, 8, 9 and 10. In a specific embodiment said binder do not bind to enkephalin peptides Met-Enkephalin depicted in SEQ ID No: 3, and Leu-Enkephalin shown in SEQ ID No: 4. In a specific embodiment said at least one binder binds to an epitope in the sequences selected from the group comprising SEQ ID No. 1, 2, 5, 6, 7, 8, 9 and 10. In another specific embodiment said at least one binder binds to an epitope with the sequences selected from the group comprising SEQ ID No. 2, 5, 6, and 10. In another very specific embodiment said binder bind to Pro-Enkephalin 119-159, Mid-regional Pro-Enkephalin-fragment, MR-PENK. In a more specific embodiment the at least one binder binds to an epitope within the amino acid sequence of Pro-Enkephalin 119-159, Mid regional Pro-Enkephalin-fragment, MR-PENK (SEQ ID No. 6) in a bodily fluid obtained from said subject, more specifically to amino acids 133-140 (SEQ ID No. 13) and/or amino acids 152-159 (SEQ ID NO. 14) wherein each of said epitopes comprises at least 4 or 5 amino acids.

Thus, according to the present methods the level of immunoreactivity of the above binder is determined in a bodily fluid obtained from said subject. Level of immunoreactivity means the concentration of an analyte determined quantitatively, semi-quantitatively or qualitatively by a binding reaction of a binder to such analyte, where preferably the binder has an affinity constant for binding to the analyte of at least $10^8$ $M^{-1}$, and the binder may be an antibody or an antibody fragment or an non-IgG scaffold, and the binding reaction is an immunoassay.

The present methods using PENK and fragments thereof, especially MR-PENK, are far superior over the methods and biomarkers used according to the prior art for predicting or monitoring the risk of development of CKD in healthy subjects, apparently healthy subjects, or patients suffering from disorders or diseases disclosed in the preceding sections (e.g. hypertension, cardiovascular disease, autoimmune disease, diabetes or metabolic syndrome, etc.).

PENK and fragments thereof as a biomarker for the before mentioned uses is a marker that is independent of inflammation. That is an important feature as most of the known kidney biomarkers like NGAL and KIM-1 are inflammation dependent, meaning if the subject has an inflammation, e.g. in sepsis, the elevation of NGAL or KIM-1 may be either due to inflammation or to kidney function/dysfunction. Thus, no differential diagnosis may be conducted, at least not by using a simple cut-off value (meaning one (1) cut-off value), which is independent from the particular patient population investigated. For NGAL and KIM-1 each and every patient has an "individual" threshold for kidney function/dysfunction depending on the inflammation status of said subject which makes clinical application of these kidney markers difficult in some diseases and impossible in others. In contrast thereto one single threshold that is independent of the inflammation status of the subject may be used according to the present methods for all subjects. This makes the present methods suitable for clinical routine in contrast to the afore-mentioned markers. PENK and fragments thereof as a biomarker in the methods of the present invention, especially MR-PENK reflects "real" kidney function. In contrast NGAL and KIM-1 reflect both, kidney damage and inflammation.

Thus, subject matter of the present invention is a method for predicting or monitoring the risk of development of CKD, wherein an inflammation status independent threshold is used.

Another advantage of the above methods and the use of PENK and fragments thereof as a biomarker is that PENK and fragments as biomarkers are very early biomarkers for kidney function, kidney dysfunction, and risk of an adverse event, success of a therapy or intervention. Very early means, e.g., that it is present in the bodily fluid of a subject with risk to develop CKD earlier than creatinine or NGAL.

Subject of the present invention is also a method for predicting or monitoring the risk of development of CKD in a subject according to any of the preceding embodiments, wherein the level of pro-Enkephalin or fragments thereof in a bodily fluid obtained from said subject either alone or in conjunction with other prognostically useful laboratory or clinical parameters is used, which may be selected from the following alternatives:
  Comparison with the median of the level of Pro-Enkephalin or fragments thereof in a bodily fluid obtained from said subject in an ensemble of predetermined samples in a population of "healthy" or "apparently healthy" subjects, preferably subjects that show no further clinical signs and/or have no laboratory markers of factors associated with an increased risk for the incidence of CKD (e.g. high systolic blood pressure, high BMI, high fasting glucose, hypertension, etc.),
  Comparison with a quantile of the level of Pro-Enkephalin or fragments thereof in a bodily fluid obtained from said subject in an ensemble of predetermined samples in a population of "healthy" or "apparently healthy" subjects as set forth above,
  Calculation based on Cox Proportional Hazards analysis or by using Risk index calculations such as the NRI (Net Reclassification Index) or the IDI (Integrated Discrimination Index).

Said additionally at least one laboratory or clinical parameter may be determined selected from the group comprising: age, gender, general health status, weight, blood sugar measurement, albumin measurement, NGAL, Cystatin C, Creatinine Clearance, Creatinin, Urea and Apache Score.

Subject matter of the invention is further an assay for determining Pro-Enkephalin and Pro-Enkephalin fragments in a sample comprising two binders that bind to two different epitopes of Pro-Enkephalin that consists of amino acids 133-140 (SEQ ID NO. 13) and amino acids 152-159 (SEQ ID NO. 14) wherein each of said epitopes comprises at least 4 or 5 amino acids. In preferred embodiments, the binders are antibodies that were prepared as set forth in PCT application PCT/EP2013/070470.

In one embodiment of the invention it may be a so-called POC-test (point-of-care), a test technology which allows performing the test within less than 1 hour near the patient without requirement of a fully automated assay system. One example for this technology is the immunochromatographic test technology.

In embodiments of the present invention, determining the level of PENK in the herein disclosed methods is preferably performed with an immunoassay. In one embodiment of the invention such an assay is a sandwich immunoassay using any kind of detection technology including but not restricted to enzyme label, chemiluminescence label, electrochemiluminescence label, preferably a fully automated assay. In one embodiment of the invention such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, Biomerieux Vidas®, Alere Triage®.

A variety of immunoassays are known and may be used for the assays and methods of the present invention, these include: radioimmunoassays ("RIA"), homogeneous enzyme-multiplied immunoassays ("EMIT"), enzyme linked immuno adsorbent assays ("ELISA"), apoenzyme reactivation immunoassay ("ARIS"), dipstick immunoassays and immuno-chromatography assays.

In one embodiment of the invention at least one of said two binders is labeled in order to be detected. The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

In a preferred embodiment said label is selected from the group comprising chemiluminescent label, enzyme label, fluorescence label, radioiodine label.

The assays can be homogenous or heterogeneous assays, competitive and non-competitive assays. In one embodiment, the assay is in the form of a sandwich assay, which is a noncompetitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person.

In the context of the present invention, fluorescence based assays comprise the use of dyes, which may for instance be selected from the group comprising FAM (5-or 6- carboxyfluorescein), VIC, NED, Fluorescein, Fluoresceinisothiocyanate (FITC), IRD-700/800, Cyanine dyes, audi as CY3, CY5, CY3.5, CY5.5, Cy7, Xanthen, 6-Carboxy-2',4', 7',4,7- hexachlorofluorescein (HEX), TET, 6-Carboxy-4,5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, Coumarines such as Umbelliferone, Benzimides, Phenanthridines, Ethidiumbromide, Acridinium dyes, Carbazol dyes, Phenoxazine dyes, Porphyrine dyes, Polymethin dyes, and the like. In the context of the present invention, chemiluminescence based assays comprise the use of dyes, based on the physical principles described for chemiluminescent materials in (24). Chemiluminescent label may be acridinium ester label, steroid labels involving isoluminol labels and the like. Preferred chemiluminescent dyes are acridinium esters.

Enzyme labels may be lactate dehydrogenase (LDH), creatine kinase (CK), alkaline phosphatase, aspartate aminotransferase (AST), alanine aminotransferase (ALT), acid phosphatase, glucose-6-phosphate dehydrogenase and so on.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-10}$.

In the context of the present invention, "binder molecules" are molecules which may be used to bind target molecules or molecules of interest, i.e. analytes (i.e. in the context of the present invention PENK and fragments thereof), from a sample. Binder molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, binder molecules may for instance be selected from the group comprising a nucleic acid molecule, a carbohydrate molecule, a PNA molecule, a protein, an antibody, a peptide or a glycoprotein. Preferably, the binder molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

In one embodiment of the invention at least one of said two binders is bound to a solid phase, such as magnetic particles, and polystyrene surfaces.

In one embodiment of the present invention, at least one of said two binders is labeled in order to be detected. Examples of labels are provided above.

In another embodiment of the present invention at least one of said two binders is bound to a solid phase. Examples of solid phases are provided above. In yet another embodiment of the present invention said label is selected from the group comprising chemiluminescent label, enzyme label, fluorescence label, radioiodine label. A further subject of the present invention is a kit comprising an assay according to the present invention wherein the components of said assay may be comprised in one or more container.

In one embodiment the subject matter of the present invention is a point-of-care device for performing a method according to the invention, wherein said POC device comprises at least one antibody or antibody fragment directed to either amino acids 133-140 (SEQ ID No. 13) or amino acids 152-159 (SEQ ID NO. 14) wherein each of said regions comprises at least 4 or 5 amino acids.

In another embodiment the subject matter of the present invention is a point-of-care device for performing a method according to the invention, wherein said POC device comprises at least two antibodies or antibody fragments directed to amino acids 133-140 (SEQ ID No. 13) and amino acids 152-159 (SEQ ID NO. 14) wherein each of said regions comprises at least 4 or 5 amino acids.

In one embodiment the subject matter of the present invention is a kit for performing a method according to the invention wherein said point of care device comprises at least one antibody or antibody fragment directed to either amino acids 133-140 (SEQ ID No. 13) or amino acids 152-159 (SEQ ID NO. 14) wherein each of said regions comprises at least 4 or 5 amino acids. In one embodiment the subject matter of the present invention is a kit for performing a method according to the invention wherein said point of care device comprises at least two antibodies or antibody fragments directed to amino acids 133-140 (SEQ ID No. 13) and amino acids 152-159 (SEQ ID NO. 14) wherein each of said regions comprises at least 4 or 5 amino acids.

EXAMPLES

Example 1—Development of Antibodies

Antibodies were prepared as set forth in PCT application PCT/EP2013/070470.

Example 2—PENK in Healthy Subjects

Healthy subjects (n=4211, average age 56 years) were measured using the MR-PENK assay. The mean value was 44.7 pmol MR-PENK pmol/L, the lowest value was 9 pmol/L and the $99^{th}$ percentile was 80 pmol/L. Since the assay sensitivity was 5.5 pmol/L, 100% of all healthy subjects were detectable using the described MR-PENK assay.

Example 3—Clinical Study and Statistical Analysis of Obtained Results

The background population for this study is the population-based prospective study from Malmö, Sweden, (Malmö Diet and Cancer Study MDCS) of which 28,098 healthy men and women born between 1923-1945 and 1923-1950 participated in the baseline examination between 1991 and 1996. The total participation rate was approximately 40.8%. Individuals from 6,103 randomly selected participants of the MDCS who underwent additional phenotyping were included, designed to study epidemiology of carotid artery disease, in the MDC Cardiovascular Cohort (MDC-CC) between 1991 and 1994. During the follow-up re-examination this random sample was re-invited to the follow-up re-examination between 2007 and 2012. 3,734 individuals of those that were alive and had not emigrated from Sweden (N=4,924) attended the follow-up re-examination. After excluding all individuals without MR-PENK levels measured at baseline (n=1,460), the association between yearly change in eGFR, plasma creatinine and plasma Cystatin C in 2,801; 2,843 and 2,978 individuals was tested, respectively, for whom measurements where available at both examinations. The relation between MR-PENK concentration at baseline and presence of CKD at follow-up re-examination was examined in a total of 2,567 participants with an eGFR of higher than 60 ml/min/1.73 $m^2$ at baseline.

All participants underwent a physical examination during baseline examination and the following anthropometric characteristics were assessed: height (cm), weight (kg), waist as well as hip circumference by trained nurses. Systolic and diastolic blood pressure (mmHG) were measured after 10 minutes of rest by trained personal. Lean body mass and body fat were estimated using a bioelectric impedance analysis (single-frequence analyses, BIA 103; JRL Systems, Detroit, Mich.). Questions concerning socio-economic status, lifestyle factors and medical history were answered by the participants via self-administrated questionnaire. Non-fasting-blood samples were drawn and immediately frozen to −80° C. and stored in a biological bank available for DNA extraction. Participant in the MDC-CC also provided fasting blood samples in which plasma creatinine (μmol/L) and cystatin C (mg/L) were measured. In addition total cholesterol (mmol/L), Triglyceride (TG)(mmol/L), low-density-lipo-cholesterol (LDL-C) (mmol/L), high-density-lipo-cholesterol (HDL-C) (mmol/L), whole blood glucose (mmol/L), plasma insulin (μIU/ml), HOMA (insulin*glucose/22.5), HbA1c (%) were quantified and blood pressure was measured in supine position with a mercury column sphygmomanometer after 10 min of rest.

During the follow-up re-examination (2007-2012) the following anthropometric characteristics were measured: height (m), weight (kg), waist and hip circumference (cm), systolic and diastolic blood pressure (SBP and DBP) (mmHG) following a similar protocol as in the baseline examination. Further concentrations of cholesterol (mmol/L), triglyceride (mmol/L), HDL-C (mmol/L), glucose (mmol/L), Creatinine (μmol/L), Cystatin C (mg/1) were quantified in fasting blood samples.

MR-PENK was measured in fasting plasma samples from 4,634 participants at MDC-CC baseline examination using the chemiluminometric sandwich immunoassay. For 1,460 individuals fasting plasma levels of MR-PENK were lacking. Those were slightly younger, had a marginal higher BMI and plasma creatinine as well as lower systolic blood pressure, fasting glucose and HbA1c-conctration at MDC baseline but did not differ in gender, plasma lipids, cystatin C or anti-hypertensive treatment frequency levels from the included participants (Supplement Table T1). To achieve normal distribution we transformed the positively skewed concentration of fasting plasma MR-PENK with the natural logarithm. Additionally, continuous MR-PENK concentrations were divided into tertiles, defining the first tertile (lowest MR-PENK concentration) as the reference. Due to the fact that women had a significantly higher mean MR-PENK concentration at baseline compared to men (one-way ANOVA P-value<0.000001), fasting plasma levels of MR-PENK were first grouped gender-specific and then these groups were combined. Both, at baseline and follow-up examination, concentrations of creatinine and cystain C were analyzed from plasma and are presented in μmol/L and mg/L, respectively. CKD was defined as presence of an estimated GFR (eGFR) of less than 60 ml/min/1.73 m$^2$ calculated according to the previously reported CKD-EPI-2012 equation which considers blood concentration of creatinine as well as cystatin C.

Statistical Analyses

Association between fasting plasma MR-PENK concentration at baseline and the risk of CKD at follow-up re-examination was analyzed using logistic regression adjusting for follow-up time in years, age, sex, GFR (ml/min/1.73 m$^2$) and for common risk factors for kidney function at baseline (systolic blood pressure, BMI (kg/m$^2$), fasting glucose and anti-hypertensive medication).

Equation 1: Example Mean Change in Weight (Kg) Per Year of Follow-Up $$\frac{\text{weight(kg)}_{\textit{follow-up re-examination}} - \text{weight(kg)}_{\textit{baseline examination}}}{\text{follow-up time (years)}}$$

SPSS (version 21, IBM) was used for the clinical epidemiological analyses and all analyses were adjusted for sex and age. Additional adjustments for covariates in specific models are reported in the results section. The null-hypothesis was rejected, if a 2-sided P-value of less than 0.05 was observed and the association was considered as statistical significant.

Cross-Sectional Analyses Between MR-PENK and Kidney Function at MDC Baseline (1991-1994)

High levels of MR-PENK were significantly associated with older age and decrease in several anthropometric characteristics in both men and women. In addition concentrations of TG, fasting plasma glucose, plasma insulin and HBbA1c decreased with increasing MR-PENK. Creatinine and cystatin C levels were significantly higher for individuals in the highest tertile (Table 1). Further adjustment of the basic model (age & sex) for BMI, body fat mass, fasting plasma glucose concentration, body lean mass, cystatin C or eGFR did not reveal that any of these covariates was driving the observed associations between MR-PENK concentration and the tested phenotypic characteristics.

TABLE 1

Cross-sectional relationship between tertiles of MR-PENK levels and phenotypic characteristics of Malmo Diet and Cancer Study participants baseline[1] (1991-1994)

| | | Fasting plasma MR-proenkephalin concentration[2] | | | |
|---|---|---|---|---|---|
| | n | Low | Medium | High | P-trend[3] |
| Age (years) | 4634 | 57.56 (0.153) | 58.04 (0.153) | 59.12 (0.153) | <0.000001 |
| BMI (kg/m$^2$) | 4630 | 26.69 (0.099) | 25.80 (0.098) | 24.96 (0.099) | <0.000001 |
| Waist (cm) | 4629 | 87.65 (0.255) | 84.85 (0.254) | 83.00 (0.255) | <0.000001 |
| SBP (mmHG) | 4634 | 144.42 (0.459) | 141.58 (0.458) | 141.334 (0.460) | 0.000002 |
| DBP (mmHG) | 4634 | 88.36 (0.237) | 87.07 (0.236) | 86.78 (0.237) | 0.000003 |
| Glucose (mmol/L)[4] | 4616 | 6.04 (0.039) | 5.71 (0.039) | 5.56 (0.039) | <0.000001 |
| Creatinine (μmol/L) | 4541 | 81.80 (0.370) | 84.73 (0.368) | 88.96 (0.370) | <0.000001 |

TABLE 1-continued

Cross-sectional relationship between tertiles of MR-PENK levels and phenotypic characteristics of Malmo Diet and Cancer Study participants baseline[1] (1991-1994)

| | | Fasting plasma MR-proenkephalin concentration[2] | | | |
|---|---|---|---|---|---|
| | n | Low | Medium | High | P-trend[3] |
| Cystatin C (mg/L) | 4310 | 0.75 (0.004) | 0.78 (0.004) | 0.83 (0.004) | <0.000001 |
| eGFR CKD-EPI 2012 | 4252 | 93.33 (0.302) | 89.82 (0.302) | 85.20 (0.305) | <0.000001 |
| Antihypertensive treatment (%) | 789 | 17.0 | 16.3 | 17.8 | /[5] |

[1]as mean and SE;
[2]gender-secific MR-PENK tertile cut-offs in pmol/L Males: low: mean 33.08 (18.30-38.50), medium: mean 42.45 (38.60-46.60), high: mean 55.45 (46.70-164.70) - Females: low: mean 37.06 (9.00-43.00), medium: mean 47.40 (43.10-51.70), high: mean 61.71 (51.80-518.10);
[3]general linear model adjusted for age and sex;
[4]fasting whole blood was converted into plasma value by multiplication with the factor 1.11; SBP = Systolic blood pressure; DBP = Diastolic blood pressure;
[5]Chi[2]-test Prospective Changes in Kidney Function at Follow-Up Re-Examination in Relation to Fasting Plasma MR-PENK Concentration at Baseline Examination Next the relation between fasting plasma MR-PENK concentration at baseline and change for phenotypic characteristics between baseline and follow-up re-examination in 2,908 participants from MDC-CC was examined. The decline in eGFR as well as the increase of cystatin C and plasma creatinine was significant in a linear model adjusted for age at follow-up, sex and corresponding baseline values. Per year of follow-up men and women classified within the highest tertile of MR-PENK concentration at baseline, eGFR declined by 1.543 ml/min/1.73 m$^2$ ($P_{trend}$<0.001), while cystatin C and plasma creatinine increased by 0.026 mg/l ($P_{trend}$<0.01) and 0.222 µmol/L ($P_{trend}$<0.00001), respectively. (Table 2).

risk increase for incidence of CKD at follow-up re-examination with increasing MR-PENK levels in a basic adjusted logistic regression model (OR: 1.165 per increase in 1 SD; $P_{trend}$=0.012). Men and women having high baseline concentration of MR-PENK had a ⅓ higher risk for incident CKD compared to individuals having low levels at baseline (OR: 1.34; 95% CI: 1.061-1.701). The association was stronger when we added further risk factor for kidney function, such as fasting plasma glucose, systolic blood pressure, anti-hypertensive medication and BMI at baseline, into the model leading to an OR of 1.236 per increase of 1 SD p-ENK concentration ($P_{trend}$<0.01). Participants with highest compared to the lowest MR-PENK levels at baseline had a 51.4% increased risk for incident CKD (95% CI 1.184-1.936). When gender-specific multivariate adjusted analysis was performed, the risk increase for high MR-

TABLE 2

Association between tertiles of fasting plasma MR-PENK at baseline examination (1991-1996) and mean changes by year in kidney function and other clinical characteristics during the follow up re-examination (2007-2012) in Malmo Diet and Cancer Study

| | | Fasting plasma MR-proenkephalin concentration | | | |
|---|---|---|---|---|---|
| | n | Low | Medium | High | P-trend[1] |
| N (%) | | 971 (33.4) | 965 (33.2) | 972 (33.2) | |
| BMI (kg/m$^2$) | 2903 | 0.080 (0.005) | 0.080 (0.005) | 0.083 (0.005) | 0.710206 |
| Waist (cm) | 2905 | 0.602 (0.015) | 0.564 (0.015) | 0.557 (0.015) | 0.033180 |
| SBP (mmHG) | 2903 | 0.270 (0.035) | 0.199 (0.035) | 0.248 (0.035) | 0.655250 |
| DBP (mmHG) | 2902 | −0.161 (0.019) | −0.194 (0.019) | −0.211 (0.019) | 0.069642 |
| Glucose (mmol/L)[2] | 2897 | 0.0045 (0.000) | 0.0042 (0.000) | 0.0039 (0.000) | 0.002307 |
| Creatinine (µmol/L) | 2767 | −0.066 (0.043) | −0.034 (0.043) | 0.222 (0.043) | 0.000003 |
| Cystatin C (mg/L) | 2636 | 0.023 (0.001) | 0.023 (0.001) | 0.026 (0.001) | 0.007428 |
| eGFR CKD-EPI 2012 | 2601 | −1.412 (0.026) | −1.412 (0.0269) | −1.543 (0.026) | 0.000593 |
| Incidence of CKD (%) | 2819 | 233 (24.4) | 298 (31.3) | 422 (44.3) | <0.0001 |

[1]in a general linear model adjusted for age at follow-up, sex and value at baseline; BSA = body surface area;
[2]Difference was calculated transferring the baseline fasting whole blood into plasma value (x factor 1.11); SBP = Systolic blood pressure; DBP = Diastolic blood pressure;

Prospective Analysis of the Association Between Fasting Plasma MR-PENK Levels at Baseline and CKD at Follow-Up Re-Examination Prevalence of CKD based on eGFR above 60 ml/min/1.73 m$^2$ was 32.3% in 2,567 participants during a median follow-up time of 16.6 years (range 13.42-20.35 years). The event rate during the follow-up time was 19.46 per 1.000 person-years and the occurrence of CKD was significantly more common in women than in men (20.93 vs. 17.31 per 1,000 person-years; X2 P-value<0.001). We observed a significant PENK concentration at baseline was comparable in women ($P_{trend}$=0.005), although in men the trend was similar but no longer significant ($P_{trend}$=0.08). However, introducing a cross product of gender and tertiles of MR-PENK concentration in the multivariate adjusted model, did not show an interaction for MR-PENK and sex ($P_{trend}$=0.99). For sensitivity analyses, prevalent patients with diabetes and CV diseases at MDC-baseline as potential risk-factors for CKD were excluded, which did not change the results in the remaining 2,452 individuals (OR=1.528 for highest MR-PENK concentration at baseline; 95% CI 1.188-1.965).

The invention claimed is:

1. A method comprising:
measuring the level of a Pro Enkephalin protein comprising the amino acid sequence of SEQ ID NO:1 or fragments thereof in a sample of bodily fluid obtained from a subject, wherein, before obtaining said sample, a prior sample of bodily fluid of said subject exhibited a level of a Pro Enkephalin protein comprising the amino acid sequence of SEQ ID NO:1 or fragments thereof above 30 pmol/L and said subject was subjected to therapeutic measures to prevent development of chronic kidney disease, wherein said fragments of Pro Enkephalin comprise the amino acid sequence of SEQ ID NO: 2, SEQ ID NO: 5, SEQ ID NO: 6, SEQ ID NO: 7, SEQ ID NO: 8, SEQ ID NO: 9, or SEQ ID NO: 10, and wherein, at the time of obtainment of said prior sample, the subject was a (i) healthy subject, or (ii) diseased subject that did not have chronic kidney disease and that had an estimated glomerular filtration rate of greater than 60 ml/min/1.73 m$^2$ for >3 months.

2. The method according to claim 1, wherein at least one additional parameter is measured for the subject and said additional parameter is selected from: age, gender, systolic blood pressure, diastolic blood pressure, anti-hypertensive treatment, body mass index, body fat mass, body lean mass, waist circumference, waist-hip-ratio, current smoker, heredity diabetes, serum creatinine level, cystatin C level, cardiovascular disease, total cholesterol, triglyceride, low-density-lipocholesterol, high-density-lipocholesterol, whole blood or plasma glucose, plasma insulin, and/or HbA$_{1c}$.

3. The method according to claim 1, wherein a group of additional parameters are measured for the subject, said group consisting of fasting glucose, systolic blood pressure, anti-hypertensive medication, and body mass index (BMI).

4. The method according to claim 1, wherein the sample of bodily fluid obtained from the subject is a blood sample, a serum sample, a plasma sample, a cerebrospinal fluid sample, a saliva sample, a urine sample or an extract of any of the aforementioned samples.

5. The method according to claim 1, wherein the bodily fluid is obtained from a non-fasting subject.

6. The method of claim 2, wherein the fragments of the Pro Enkephalin each comprise the amino acid sequence of SEQ ID NO: 2, SEQ ID NO: 5, SEQ ID NO: 6, or SEQ ID NO: 10.

7. The method according to claim 1, wherein the prior sample of bodily fluid was measured by an immunoassay with a sensitivity of <15pmol/L.

8. The method according to claim 1, wherein the bodily fluid is obtained from a fasting subject.

9. A method for preparing a sample comprising:

obtaining a sample of bodily fluid from a subject; and adding to said sample, a binder that binds to a Pro Enkephalin protein comprising the amino acid sequence of SEQ ID NO:1, or one or more fragments thereof, wherein said one or more fragments comprise the amino acid sequence of SEQ ID NO: 2, SEQ ID NO: 5, SEQ ID NO: 6, SEQ ID NO: 8, SEQ ID NO: 9, SEQ ID NO: 10 or SEQ ID NO: 11, wherein, at the time of obtaining said sample, the subject is a (i) healthy subject, or (ii) diseased subject that does not have chronic kidney disease, and that has had an estimated glomerular filtration rate of greater than 60 ml/min/1.73 m$^2$ for >3 months, and wherein in said sample, said binder is bound to the Pro Enkephalin or one or more of said fragments at a level above 30 pmol/L.

10. The method of claim 9, wherein said binder is bound to the Pro Enkephalin or one or more of said fragments at a level of between 30 to and 80 pmol/L.

11. The method according to claim 9, wherein said binder is bound to the Pro Enkephalin or one or more of said fragments at a level above 49 pmol/L.

12. The method of claim 9, wherein said binder is bound to the Pro Enkephalin or one or more of said fragments at a level of 35 pmol/L or above.

13. The method of claim 9, wherein said binder is bound to the Pro Enkephalin or one or more of said fragments at a level of 40 pmol/L or above.

14. The method of claim 9, wherein said binder is bound to the Pro Enkephalin or one or more of said fragments at a level of 41 pmol/L or above.

* * * * *